(12) United States Patent
Silverman (10) Patent No.: US 7,431,586 B1
(45) Date of Patent: Oct. 7, 2008

(54) ADJUSTABLE ORTHODONTIC APPLIANCE (76) Inventor: Mitchell B. Silverman, 8520 Snakedance Dr. NE., Albuquerque, NM (US) 87111

( * ) Notice: Subject to any disclaimer, the term of this patent is extended or adjusted under 35 U.S.C. 154(b) by 162 days.

(21) Appl. No.: 11/437,199

(22) Filed: May 19, 2006

(51) Int. Cl.
*A61C 3/00* (2006.01)
(52) U.S. Cl. .......................................... 433/9
(58) Field of Classification Search .............. 433/8, 433/9, 16, 23
See application file for complete search history.

(56) References Cited

U.S. PATENT DOCUMENTS

| | | | | |
|---|---|---|---|---|
| 3,421,221 A * | 1/1969 | Silverman et al. | | 433/8 |
| 3,423,833 A * | 1/1969 | Pearlman | | 433/16 |
| 3,494,034 A | 2/1970 | Kesling | | |
| 3,792,529 A | 2/1974 | Goshgarian | | |
| 4,139,945 A | 2/1979 | DiGiulio | | |
| 4,171,568 A | 10/1979 | Förster | | |
| 4,243,387 A | 1/1981 | Prins | | |
| 4,353,692 A * | 10/1982 | Karrakussoglu | | 433/16 |
| 4,427,381 A * | 1/1984 | Hall | | 433/14 |
| 4,487,581 A * | 12/1984 | Adler | | 433/16 |
| 4,597,739 A * | 7/1986 | Rosenberg | | 433/16 |
| 4,676,746 A | 6/1987 | Klapper | | |
| 4,815,968 A | 3/1989 | Keller | | |
| 5,302,121 A | 4/1994 | Gagin | | |
| 5,762,492 A | 6/1998 | Kanomi et al. | | |
| 5,816,800 A | 10/1998 | Brehm et al. | | |
| 5,954,502 A | 9/1999 | Tuenge et al. | | |
| 7,306,458 B1 * | 12/2007 | Lu | | 433/16 |
| 2005/0003324 A1 | 1/2005 | Reising | | |
| 2005/0048433 A1 | 3/2005 | Hilliard | | |
| 2007/0092849 A1 * | 4/2007 | Cosse | | 433/8 |

FOREIGN PATENT DOCUMENTS

| | | |
|---|---|---|
| JP | 2002209914 A | 7/2002 |
| WO | WO 97/15241 | 5/1997 |

* cited by examiner

*Primary Examiner*—Ralph A Lewis
(74) *Attorney, Agent, or Firm*—Workman Nydegger (57) ABSTRACT

This disclosure relates to an orthodontic appliance having a bracket that can be readily adjusted after the orthodontic appliance is attached to a tooth. In one example embodiment, an adjustable orthodontic appliance includes a base, a bracket, and a spring-loaded locking mechanism attached to the bracket. In this example embodiment, the spring-loaded locking mechanism has a locked state where the spring-loaded locking mechanism engages with the base such that the position of the bracket is locked in place with respect to the position of the base. The spring-loaded locking mechanism also has an unlocked state where the spring-loaded locking mechanism disengages from the base such that the position of the bracket is adjustable with respect to the position of the base.

23 Claims, 7 Drawing Sheets

ADJUSTABLE ORTHODONTIC APPLIANCE

BACKGROUND OF THE INVENTION

1. The Field of the Invention

Embodiments of the invention relate to an adjustable orthodontic appliance. More particularly, embodiments of the invention relate to an orthodontic appliance having an adjustable bracket.

2. The Relevant Technology

Orthodontic appliances are used by orthodontists to change the way a patient's mouth and teeth are growing. One type of orthodontic appliance is an orthodontic bracket. A typical orthodontic bracket is a metal or ceramic appliance that is attached to a tooth, for example, by bonding the bracket to the tooth using an orthodontic adhesive. After a series of brackets are attached to adjoining teeth, a flexible archwire is secured to the series of brackets, thus placing forces on the teeth to move and adjust their position. Over time, the wire moves the teeth by causing the brackets on adjoining teeth to align. As the brackets and teeth align, the orthodontist will progressively replace the flexible archwire with stiffer archwires until the desired result is achieved.

Precise bracket placement is critical to this process. In particular, since the objective of the treatment is to align the teeth, it is critical that the brackets are attached to the teeth in the precise position such that when the archwire ultimately aligns the brackets, the teeth will also be aligned. Thus, bracket placement on each tooth will determine the final position of the teeth. If the brackets are not aligned correctly, then the orthodontic treatment will not ultimately result in correctly aligned teeth.

One of the more difficult and time consuming tasks for an orthodontist is correct bracket placement. During a typical treatment program, an orthodontist may need to detach one or more brackets because an original or subsequent attachment of the bracket was incorrect. Difficulties associated with bracket attachment methods and difficulties associated with estimating the correct placement for each bracket can make correct bracket placement very difficult on the first attempt, or even the second attempt. Where a bracket is not placed correctly, it must be detached from the tooth and reattached with correct placement. The detachment and reattachment of brackets during a typical orthodontic treatment program can be costly in terms of time and materials. The difficulties involved in the initial placement of a bracket can also make subsequent attempts at bracket placement complicated and time-consuming.

BRIEF SUMMARY OF SOME EXAMPLE EMBODIMENTS OF THE INVENTION

These and other limitations are overcome by example embodiments of the invention, which relate to an adjustable orthodontic appliance and, more particularly, to an orthodontic appliance having an adjustable bracket.

In one example embodiment, an adjustable orthodontic appliance includes a base, a bracket, and a spring-loaded locking mechanism attached to the bracket. In this example embodiment, the spring-loaded locking mechanism has a locked state where the spring-loaded locking mechanism engages with the base such that the position of the bracket is locked in place with respect to the position of the base. The spring-loaded locking mechanism also has an unlocked state where the spring-loaded locking mechanism disengages from the base such that the position of the bracket is adjustable with respect to the position of the base.

In another example embodiment, an adjustable orthodontic appliance includes a base comprising a surface adapted to be attached to a tooth and a mesh surface; a bracket comprising one or more notches adapted to receive an arch wire, the bracket also defining a hollow cavity; and a spring-loaded locking mechanism at least partially disposed within the hollow cavity of the bracket. In this example embodiment, the spring-loaded locking mechanism includes at least one leaf spring and one or more pins operably connected to the at least one leaf spring. In this example embodiment, the at least one leaf spring, when naturally uncompressed, causes the one or more pins to engage with the mesh surface of the base thereby locking the position of the bracket in place with respect to the position of the base. Also in this example embodiment, the at least one leaf spring, when manually compressed, causes the one or more pins to disengage from the mesh surface of the base, thereby allowing the position of the bracket to be adjusted with respect to the position of the base.

In yet another example embodiment, an adjustable orthodontic appliance includes a base comprising a surface adapted to be attached to a tooth and a mesh surface; a bracket comprising one or more notches adapted to receive an arch wire; and a spring-loaded locking mechanism at least partially attached to the bracket. In this example embodiment, the spring-loaded locking mechanism includes at least one helical compression spring and one or more pins operably connected to the at least one helical compression spring. In this example embodiment, the at least one helical compression spring, when naturally uncompressed, causes the one or more pins to engage with the mesh surface of the base thereby locking the position of the bracket in place with respect to the position of the base. Also in this example embodiment, the at least one helical compression spring, when manually compressed, causes the one or more pins to disengage from the mesh surface of the base, thereby allowing the position of the bracket to be adjusted with respect to the position of the base.

These and other aspects of example embodiments of the present invention will become more fully apparent from the following description and appended claims.

BRIEF DESCRIPTION OF THE DRAWINGS

To further clarify certain aspects of the present invention, a more particular description of the invention will be rendered by reference to specific embodiments thereof which are disclosed in the appended drawings. It is appreciated that these drawings depict only example embodiments of the invention and are therefore not to be considered limiting of its scope. Aspects of the invention will be described and explained with additional specificity and detail through the use of the accompanying drawings in which.

DETAILED DESCRIPTION OF EXAMPLE EMBODIMENTS OF THE INVENTION

Example embodiments of the invention disclosed herein relate to an adjustable orthodontic appliance and, more particularly, to an orthodontic appliance having an adjustable bracket. The adjustable bracket can be repeatedly repositioned with respect to a tooth even after the orthodontic appliance has been permanently attached to the tooth. This adjustability helps to overcome the difficulties associated with precise bracket positioning in orthodontic treatment. Reference will now be made to the drawings which disclose various aspects of exemplary embodiments of the invention. It is to be understood that the drawings are diagrammatic and schematic representations of such exemplary embodiments, and are not limiting of the present invention, nor are they necessarily drawn to scale.

I. Exemplary Adjustable Orthodontic Appliance

Figure 1A:
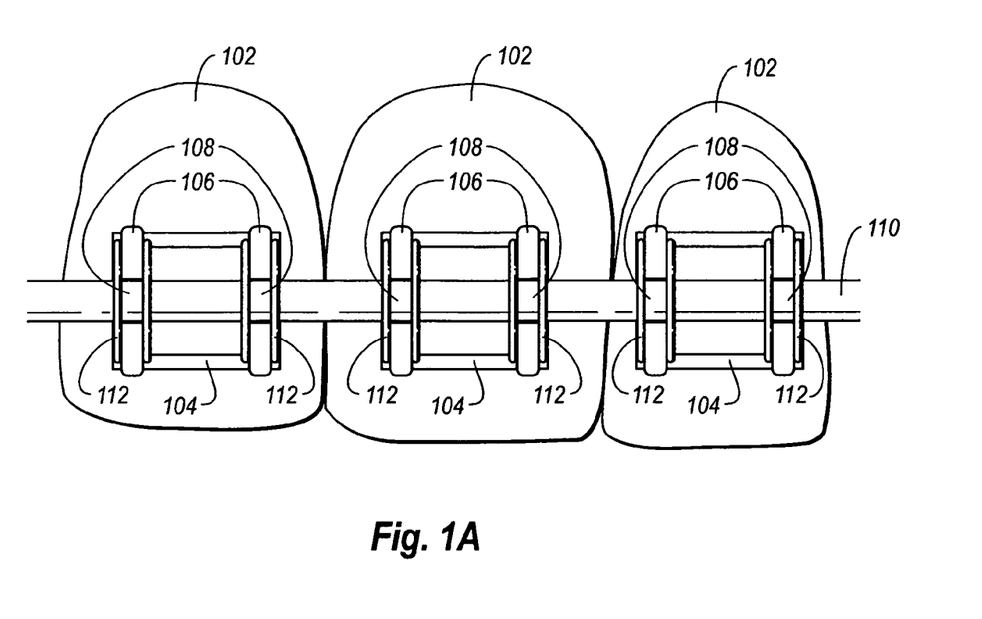
FIG. 1A is a front view of three example adjustable orthodontic appliances as installed on three adjoining teeth.

Turning now to FIG. 1A, aspects of three example adjustable orthodontic appliances are disclosed. The three identical adjustable orthodontic appliances of FIG. 1A can be used in conjunction with other orthodontic appliances in the course of an orthodontic treatment program. Each of the three teeth 102 in FIG. 1A are undergoing an orthodontic treatment that is intended to ultimately result in the alignment of the teeth 102. This treatment includes attaching an adjustable orthodontic appliance 104 to each tooth. Each adjustable orthodontic appliance 104 includes four wings 106 which have two functions. First, the four wings 106 cooperate to define two notches 108 that are configured to receive a flexible arch wire 110. Second, each pair of wings 106 provides a convenient structure to which an elastic band 112 can be attached in order to maintain the flexible archwire 110 in the notches 108. During the course of orthodontic treatment, flexible archwires with increasing stiffness are installed in each of the brackets 104 in order to cause the teeth 102 to align.

Figure 1B:
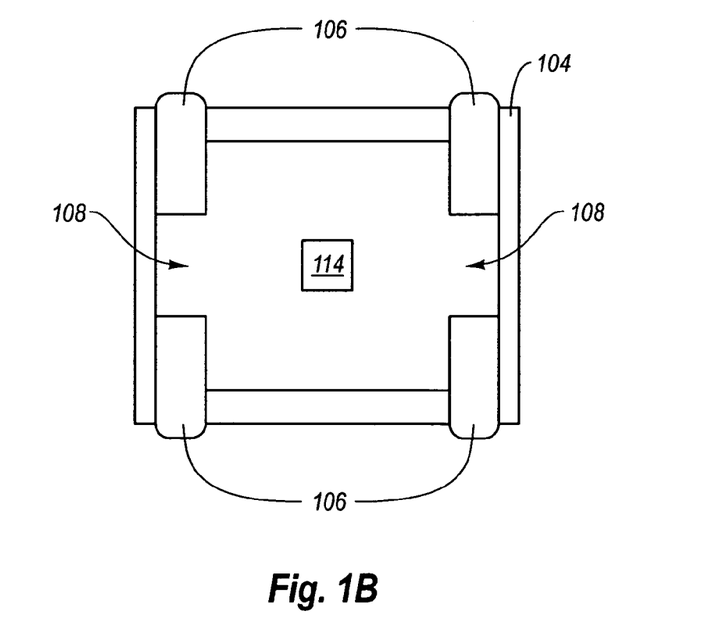
FIG. 1B is a front view of one of the example adjustable orthodontic appliances of FIG. 1A.

With reference now to FIG. 1B, further aspects regarding the bracket 104 are disclosed. Specifically, FIG. 1B discloses bracket 104 in an uninstalled state without a flexible archwire being present in the notches 108. FIG. 1B also discloses an opening 114 through which an instrument can be inserted in order to access a spring-loaded locking mechanism. Example embodiments of the spring-loaded locking mechanism are disclosed in greater detail herein in connection with FIGS. 2A-3E. As disclosed in FIG. 1B, the opening 114 is positioned in the center of the bracket 104 and is only accessible where bracket 104 does not have an archwire installed in notches 108. However, the opening 114 can alternatively be positioned off center such that the opening 114 can be accessed even where bracket 104 does have an archwire installed in notches 108. In addition, the opening 114 can vary in size and shape and still be suitable for providing access to a spring-loaded locking mechanism.

II. Exemplary Leaf Spring Embodiment

Figure 2A:
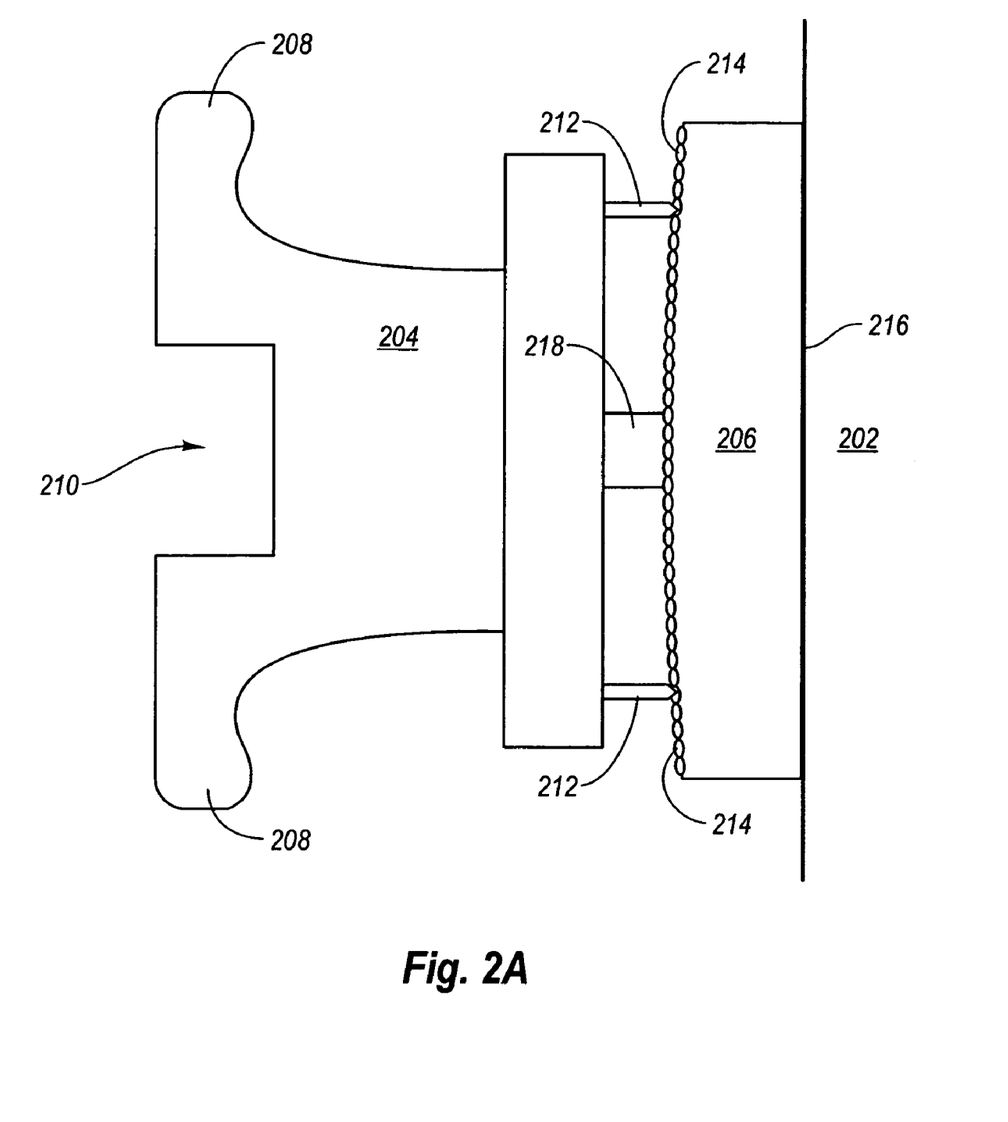
FIG. 2A is a side view of one example embodiment of an adjustable orthodontic appliance having a spring-loaded locking mechanism as installed on a tooth.

Turning now to FIG. 2A, aspects of an exemplary embodiment of an adjustable orthodontic appliance are disclosed. The adjustable orthodontic appliance of FIG. 2A includes all of the aspects disclosed in FIGS. 1A and 1B. In addition, the adjustable orthodontic appliances of FIG. 2A includes an exemplary leaf spring embodiment of a spring-loaded locking mechanism that allows the position of the orthodontic appliance to be adjusted even after being attached to a tooth 202. The adjustable orthodontic appliance includes a bracket 204 and a base 206. The bracket 204 also includes wings 208 and notches 210 configured to receive an archwire and maintain the archwire in place using elastic bands or other suitable materials such as string or wire.

The bracket 204 also includes a spring-loaded locking mechanism that enables the position of bracket 204 to be adjusted with respect to the position of the base 206. The spring-loaded locking mechanism includes pins 212 which extend down out of the bracket 204. The pins 212 are sized and positioned to engage a mesh covered surface 214 of the base 206. As discussed in greater detail in connection with FIGS. 2B and 2C, each of pins 212 is spring-loaded such that one or more springs bias each pin against the mesh covered surface 214. Simultaneously, a post 218 pivotally attaches the bracket 204 to the base 206. The simultaneous pressure of the pins 212 against the base 206 and the pivotal attachment of the post 218 to the bracket 204 results in the position of the bracket 204 being locked with respect to the position of the base 206.

A bonding surface 216 of the base 206 is configured to be attached to a tooth 202, for example, by bonding using an orthodontic adhesive. Alternatively, the bonding surface 216 can be configured to wrap around the tooth 202, or partially wrap around the tooth 202, in which case the base 206 can be attached to the tooth 202 by molding the shape of the bonding surfaces to the contours of the tooth 202.

Figure 2B:
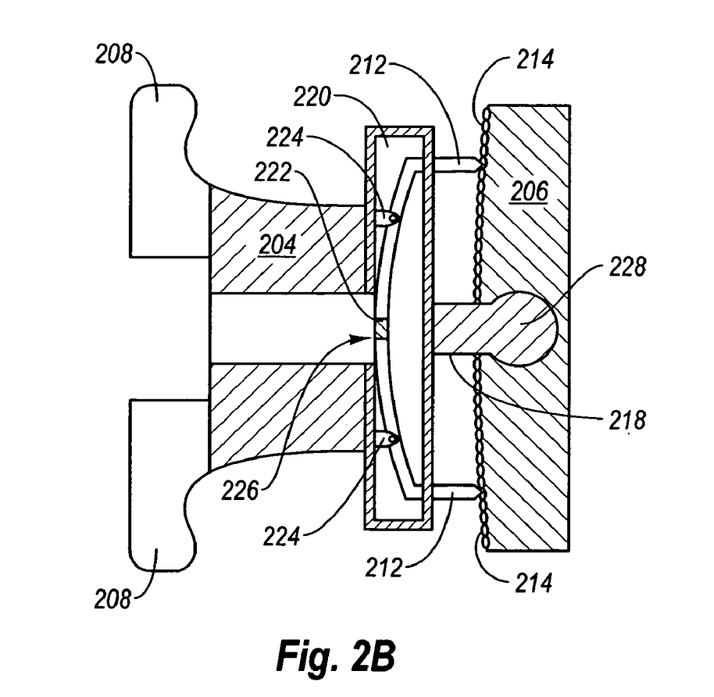
FIG. 2B is a cross-sectional side view of the adjustable orthodontic appliance of FIG. 1A with the spring-loaded locking mechanism in a locked state.
Figure 2C:
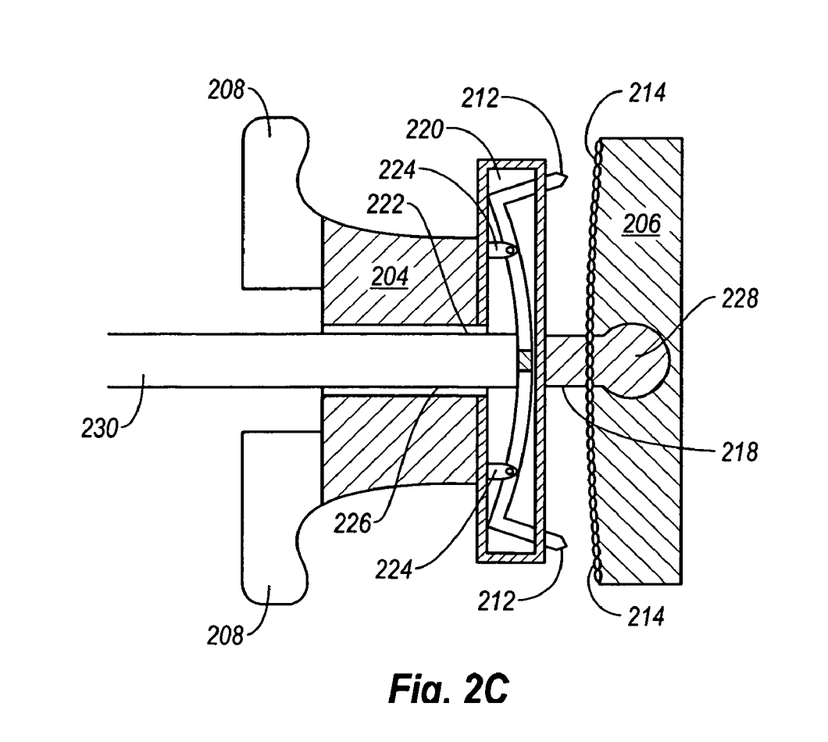
FIG. 2C is a cross-sectional side view of the adjustable orthodontic appliance of FIG. 1A with the spring-loaded locking mechanism in an unlocked state.

With reference now to FIGS. 2B and 2C, additional aspects of the adjustable orthodontic appliance of FIG. 2A are disclosed. In particular, FIGS. 2B and 2C disclose additional aspects of the spring-loading locking mechanism of the adjustable orthodontic appliance of FIG. 2A. As disclosed in FIGS. 2B and 2C, the spring-loading locking mechanism is partially disposed within a hollow cavity 220 defined in the bracket 204. The spring-loading locking mechanism includes one or more leaf springs 222. Each of the one or more leaf springs 222 is attached to a hinged fulcrum 224 and a pin 212. The hinged fulcrum 224 is the means whereby the spring-loaded locking mechanism is attached to the bracket 204.

When the one or more leaf springs 222 are naturally uncompressed, the one or more leaf springs 222 cause the pins 212 to engage with the mesh surface 214 of the base 206, thereby locking the position of the bracket 204 in place with respect to the position of the base 206. The bracket 204 also includes an opening 226, which corresponds to the opening 114 of FIG. 1B, which enables access to the one or more leaf springs 222. As disclosed in FIG. 2C, when an instrument 230 is inserted into the opening 226 in order to manually compress the one or more leaf springs 222, the compression of the one or more leaf springs 222 causes the pins 212 to disengage from the mesh surface 214 of the base 206 and retract into the hollow cavity 220. While the pins 212 disengaged from the mesh surface 214, the position of the bracket 204 can be adjusted with respect to the position of the base 206.

When an instrument 230 is inserted into the opening 226 thereby allowing the position of the bracket 204 to be adjusted with respect to the position of the base 206, the post 218 maintains the bracket 204 pivotally attached to base 206. As disclosed in FIGS. 2B and 2C, the post 218 includes a ball 228 which fits in a socket 232 of the base 206. This ball-and-socket joint allows the bracket 204 to pivot from one position to another when the bracket 204 is unlocked from the base 206 without the bracket 204 becoming fully detached from the base 206. Other types of pivotal joints or attachments can be used in place of the ball-and-socket joint disclosed in FIGS. 2B and 2C as long as the pivotal joints or attachments allow the position of the bracket 204 to be repositioned with respect to the position of the base 206, including the cufflink joint disclosed herein in connection with FIGS. 3B-3E.

Figure 2D:
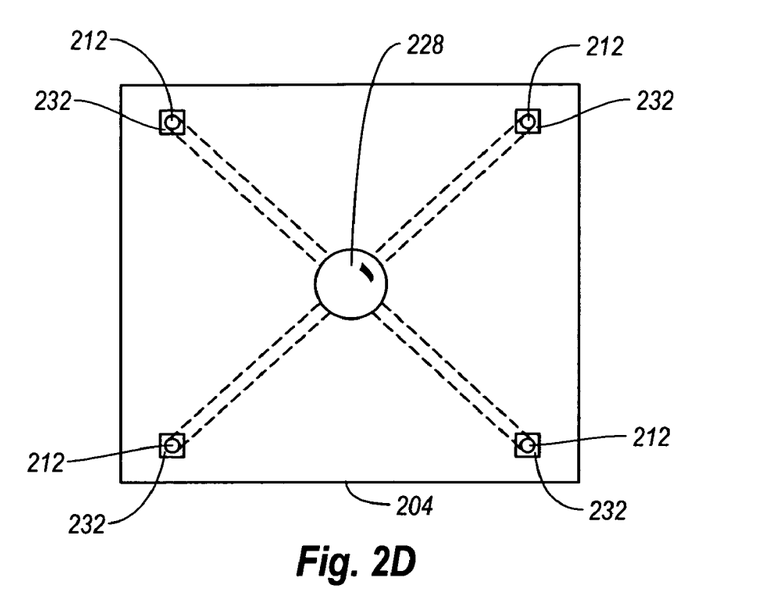
FIG. 2D is a back view of the bracket of the adjustable orthodontic appliance of FIG. 1A.
Figure 2E:
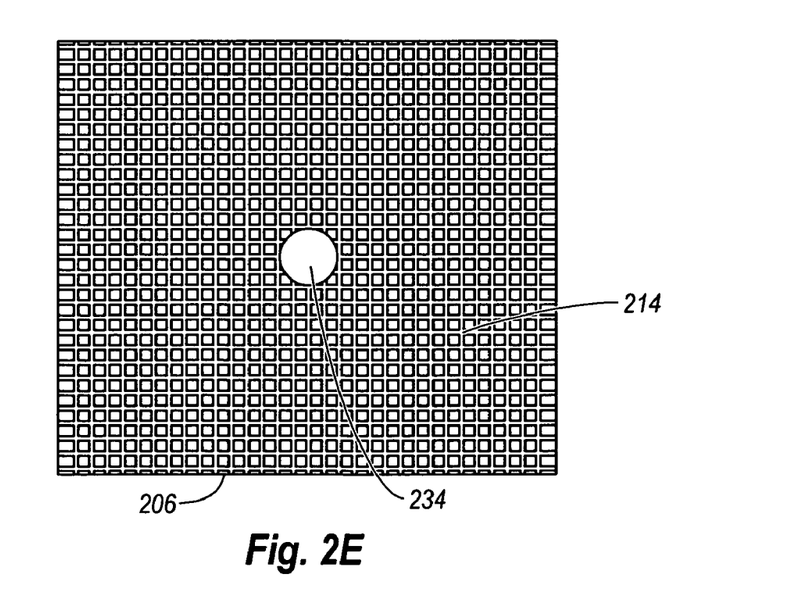
FIG. 2E is a front view of the base of the adjustable orthodontic appliance of FIG. 1A.

With reference now to FIGS. 2D and 2E, additional aspects of the adjustable orthodontic appliance of FIG. 2A are disclosed. In particular, FIG. 2D discloses a back view of the bracket 204 and FIG. 2E discloses a front view of the base 206. The ball 228 is attached to the post 219 (not shown) is positioned in the center of the bracket 204 and a corresponding socket 234 is positioned in the center of the base 206. The pins 212 are shown extending outward from openings 232 in the back of the bracket 204. Although four pins 212 are illustrated in FIG. 2D, a greater number of pins can be included in the spring-loaded locking mechanism for greater stability. Conversely, fewer than four pins could be used for decreased complexity, cost, and weight. The pins 212 are designed and positioned to releasably engage the mesh surface 214 on base 206 when the ball 228 is positioned in the socket 234.

The pins 212 can engage the mesh surface 214 in a number of ways including, by way of example, friction between pins 212 and the mesh surface 214 or a magnetic force between pins 212 and the mesh surface 214. In the case of friction, the indentations in the mesh surface 214 can be sized and configured to receive the heads of the pins 212 and hold the pins 212 in place. In the case of magnetic force, the mesh surface can optionally include indentations but necessarily be formed from a material that exerts an attractive force on the material from which the pins 214 are formed. In either example, when the pins 212 are lifted away from the mesh surface 214, the pins 212 become disengaged from the mesh surface 214 either because there is no longer friction between the pins 212 and the mesh surface 214 or because the distance between the pins 212 and the mesh surface 214 is great enough to overcome the magnetic force between the pins 212 and the mesh surface 214. Disengaging the pins 212 from the mesh surface 214 unlocks the position of the bracket 204 with respect to the position of the base 206.

Although the bracket 204 and the base 206 are disclosed having a generally rectangular shape, other shapes are possible. Similarly, the openings 226 and 232 can have a shape other than the rectangular shape disclosed in FIGS. 2B and 2C.

III. Exemplary Helical Compression Spring Embodiment

Figure 3A:
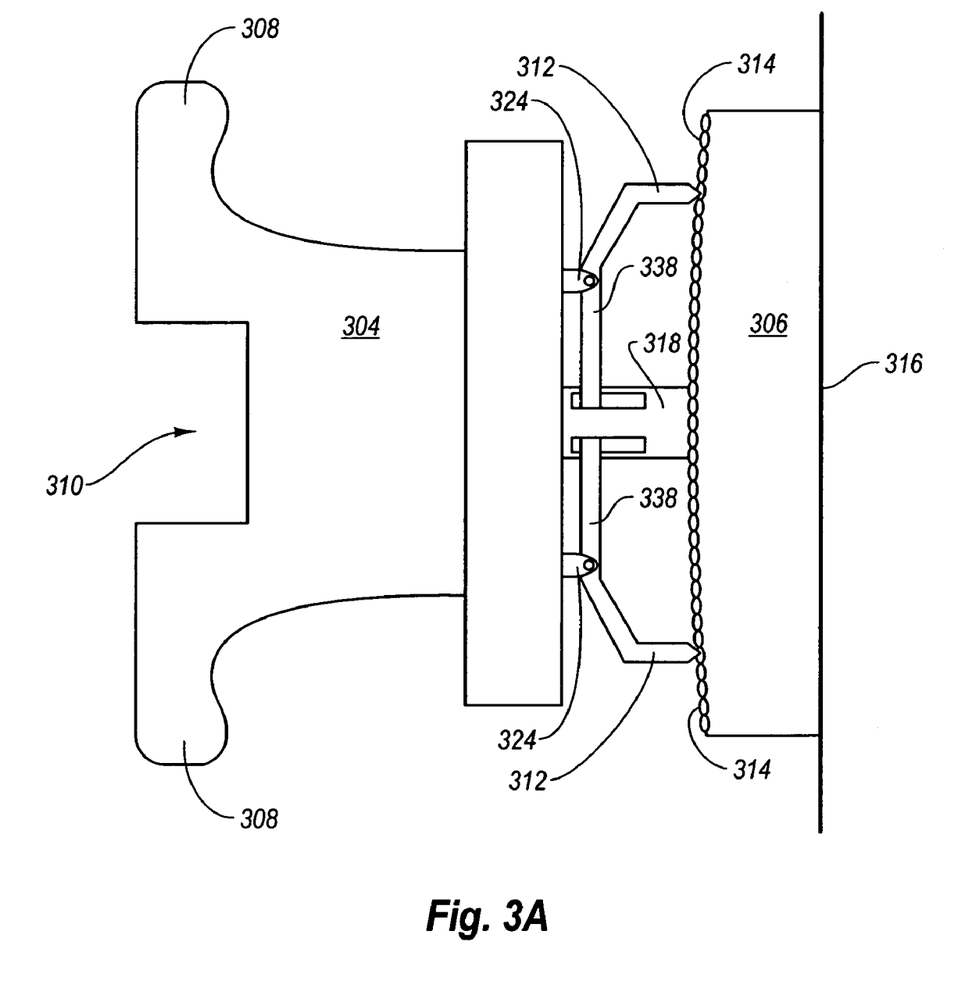
FIG. 3A is a side view of one example embodiment of an adjustable orthodontic appliance having a spring-loaded locking mechanism as installed on a tooth.

Turning now to FIG. 3A, aspects of another exemplary embodiment of an adjustable orthodontic appliance are disclosed. The adjustable orthodontic appliance of FIG. 3A includes all of the aspects of the adjustable orthodontic appliance disclosed in FIGS. 1A and 1B. In addition, the adjustable orthodontic appliances of FIG. 3A includes an exemplary helical compression spring embodiment of a spring-loaded locking mechanism that allows the position of the orthodontic appliance to be adjusted even after being attached to a tooth 302. The adjustable orthodontic appliance includes a bracket 304 and a base 306. The bracket 304 includes wings 308 and notches 310 configured to receive an archwire and maintain the archwire in place using elastic bands or other suitable materials.

The bracket 304 also includes a spring-loaded locking mechanism that enables the position of bracket 304 to be adjusted with respect to the position of the base 306. The spring-loaded locking mechanism includes pins 312. The pins 312 are attached to lever arms 338. The lever arms 338 are attached to the bracket 304 at hinged fulcrums 324. The pins 312 are sized and positioned to engage a mesh covered surface 314 of the base 306. As disclosed in greater detail in connection with FIGS. 3B and 3C, each of the pins 312 is spring-loaded such that one or more springs bias each pin against the mesh covered surface 314. Simultaneously, a post 318 pivotally connects the bracket 304 to the base 306. The simultaneous pressure of the pins 312 against the base 306 and the pivotal attachment of the post 318 to the bracket 304 results in the position of the bracket 304 being locked with respect to the position of the base 306. A bonding surface 316 of the base 306 can be attached to a tooth 302, as disclosed herein in connection the bonding surface 216 and the base 206 of FIG. 2A.

Figure 3B:
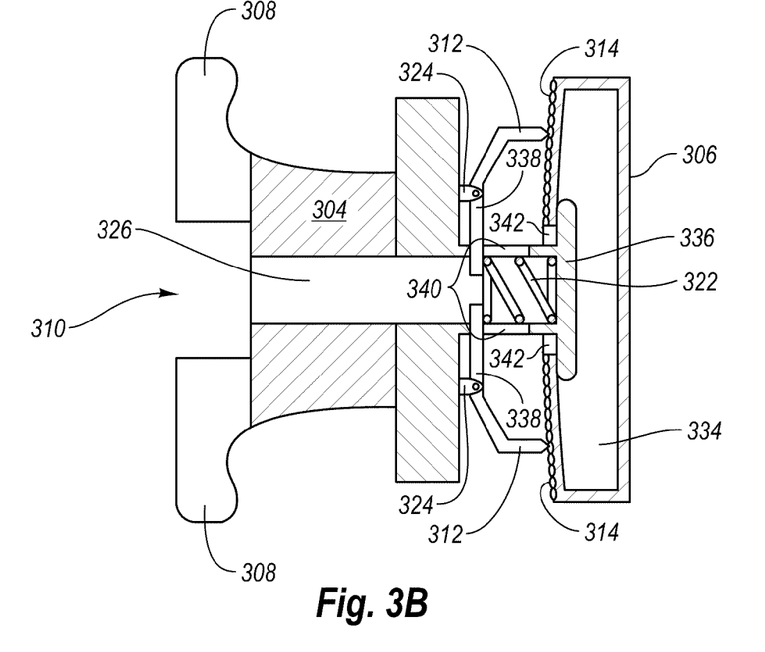
FIG. 3B is a cross-sectional side view of the adjustable orthodontic appliance of FIG. 3A with the spring-loaded locking mechanism in a locked state.
Figure 3C:
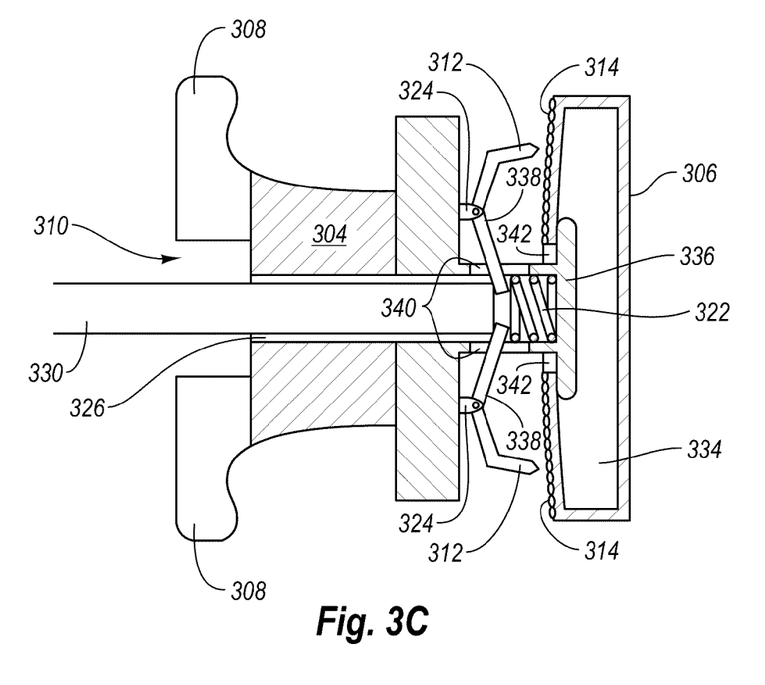
FIG. 3C is a cross-sectional side view of the adjustable orthodontic appliance of FIG. 3A with the spring-loaded locking mechanism in an unlocked state.

With reference now to FIGS. 3B and 3C, additional aspects of the adjustable orthodontic appliance of FIG. 3A are disclosed. In particular, FIGS. 3B and 3C disclose additional aspects of the spring-loading locking mechanism of the adjustable orthodontic appliance of FIG. 3A. As disclosed in FIGS. 3B and 3C, the lever arms 338 of the spring-loading locking mechanism are attached to the bracket 304 at hinged fulcrums 324. Another portion of the spring-loaded locking mechanism, one or more helical compression springs 322, is disposed within a hollow cavity defined within the post 318. Each of the one or more helical compression springs 322 is attached to each of lever arms 338.

When the one or more helical compression springs 322 is naturally uncompressed, the one or more helical compression springs 322 cause the pins 312 to engage with the mesh surface 314 of the base 306, thereby locking the position of the bracket 304 in place with respect to the position of the base 306. The bracket 304 also includes an opening 326, which corresponds to the opening 114 of FIG. 1B, which enables access to the or more helical compression springs 322. As disclosed in FIG. 3C, when an instrument 330 is inserted into the opening 326 in order to manually compress the one or more helical compression springs 322, the compression of the one or more helical compression springs 322 causes the lever arms 338 to rotate about the hinged fulcrums 324 thereby lifting pins 312 and causing pins 312 to disengage from the mesh surface 314 of the base 306. While the pins 312 are disengaged from the mesh surface 314, the position of the bracket 304 can be adjusted with respect to the position of the base 306.

When an instrument 330 is inserted into the opening 326 thereby allowing the position of the bracket 304 to be adjusted with respect to the position of the base 306, the post 318 maintains the bracket 304 pivotally attached to the base 306. As disclosed in FIGS. 3B and 3C, the post 318 includes a button 336 which fits in a hollow cavity 334 of the base 306. The button 336 acts as a cufflink within the hollow cavity 334 to maintain the bracket 304 pivotally attached to the base 306. This cufflink joint allows the bracket 304 to pivot from one position to another when the bracket 304 is unlocked from the base 306 without the bracket 304 becoming fully detached from the base 306. Other types of pivotal joints or attachments can be used in place of the cufflink joint disclosed in FIGS. 3B and 3C, as long as the pivotal joints or attachments allow the position of the bracket 304 to be repositioned with respect to the position of the base 306, including the ball-and-socket joint disclosed herein in connection with FIGS. 2B-2E.

Figure 3D:
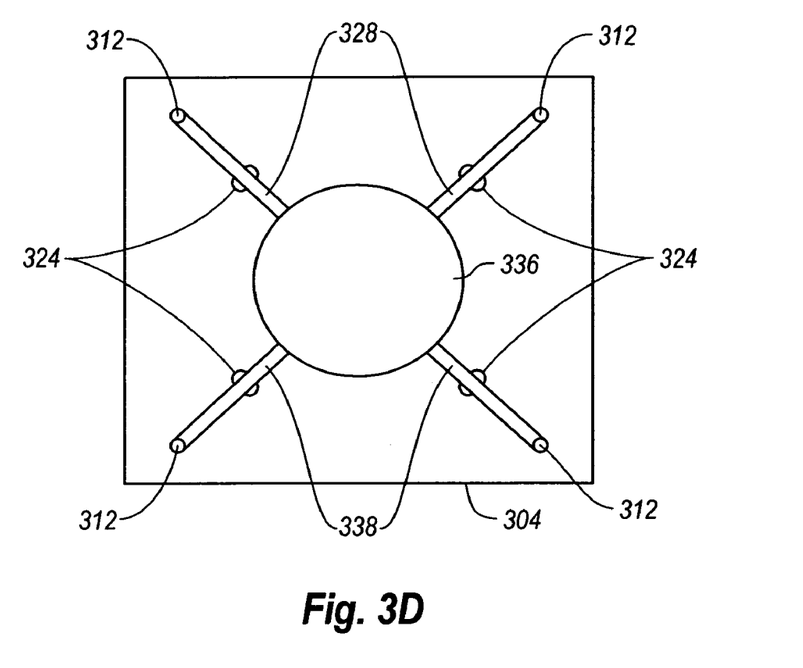
FIG. 3D is a back view of the bracket of the adjustable orthodontic appliance of FIG. 3A.
Figure 3E:
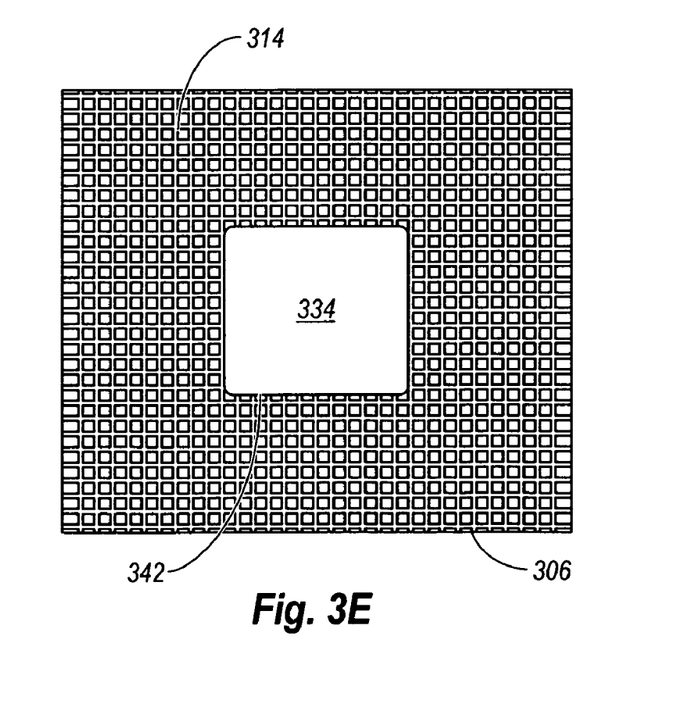
FIG. 3E is a front view of the base of the adjustable orthodontic appliance of FIG. 3A.

With reference now to FIGS. 3D and 3E, additional aspects of the adjustable orthodontic appliance of FIG. 3A are disclosed. In particular, FIG. 3D discloses a back view of the bracket 304 and FIG. 3E discloses a front view of the base 306. The button 336 that is attached the post 318 (not shown) is positioned in the center of the bracket 304 and a corresponding hollow cavity 334 with an opening 342 is positioned in the center of the base 306. Four pins 312 are shown extending outward from four lever arms 338, although greater or less than four pins and pivot arms can be included. The lever arms 338 are shown attached to hinged fulcrums 324 on the back of the bracket 304. The pins 312 are designed and positioned to releasably engage the mesh surface 314 on base 306 when the button 336 is positioned in the hollow cavity 334, as disclosed herein in connection with FIGS. 2D and 2E.

The exemplary embodiments of an adjustable orthodontic appliance disclosed in FIGS. 2A-3A and 3A-3E, in connection with FIGS. 1A and 1B, are therefore configured with an adjustable bracket that can be repeatedly repositioned with respect to a base even after the base has been permanently attached to the tooth. This adjustability helps to overcome the difficulties associated with precise bracket positioning in orthodontic treatment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An adjustable orthodontic appliance comprising:
    a base;
    a bracket; and
    a spring-loaded locking mechanism attached to the bracket, the spring-loaded locking mechanism having:
        a locked state where the spring-loaded locking mechanism engages with the base such that the position of the bracket is locked in place with respect to the position of the base; and
        an unlocked state where the spring-loaded locking mechanism disengages from the base such that the position of the bracket is adjustable with respect to the position of the base.

2. The adjustable orthodontic appliance as recited in claim 1, wherein a surface of the base is adapted to be attached to a tooth.

3. The adjustable orthodontic appliance as recited in claim 2, wherein the surface of the base is further adapted to be bonded to a tooth.

4. The adjustable orthodontic appliance as recited in claim 2, wherein the surface of the base is further adapted to at least partially wrap around a tooth.

5. The adjustable orthodontic appliance as recited in claim 1, wherein the bracket defines one or more notches for receiving an arch wire.

6. The adjustable orthodontic appliance as recited in claim 5, wherein the bracket comprises one or more wings for attaching elastic bands in order to maintain the arch wire in the one or more notches.

7. The adjustable orthodontic appliance as recited in claim 1, wherein the bracket defines an opening through which an instrument can be inserted in order to unlock the spring-loaded locking mechanism.

8. The adjustable orthodontic appliance as recited in claim 1, wherein the bracket is pivotally connected to the base such that when the spring-loaded locking mechanism is in the unlock state the bracket and the base remain pivotally connected.

9. The adjustable orthodontic appliance as recited in claim 1, wherein the spring-loaded locking mechanism comprises:
    at least one spring; and
    one or more pins operably connected to the at least one spring.

10. The adjustable orthodontic appliance as recited in claim 9, wherein the one or more pins engage a mesh surface of the base when the spring-loaded locking mechanism is in the locked state, and wherein the one or more pins do not engage the mesh surface of the base when the spring-loaded locking mechanism is in the unlocked state.

11. The adjustable orthodontic appliance as recited in claim 9, wherein the one or more pins engage the mesh surface by a magnetic force between the one or more pins and the mesh surface.

12. An adjustable orthodontic appliance comprising:
    a base comprising a surface adapted to be attached to a tooth and a mesh surface;
    a bracket comprising one or more notches adapted to receive an arch wire, the bracket also defining a hollow cavity; and
    a spring-loaded locking mechanism at least partially disposed within the hollow cavity of the bracket, the spring-loaded locking mechanism comprising:
        at least one leaf spring; and
        one or more pins operably connected to the at least one leaf spring,
    wherein the at least one leaf spring, when naturally uncompressed, causes the one or more pins to engage with the mesh surface of the base thereby locking the position of the bracket in place with respect to the position of the base, and
    wherein the at least one leaf spring, when manually compressed, causes the one or more pins to disengage from the mesh surface of the base, thereby allowing the position of the bracket to be adjusted with respect to the position of the base.

13. The adjustable orthodontic appliance as recited in claim 12, wherein the bracket further comprises one or more wings for attaching elastic bands in order to maintain the arch wire in the one or more notches.

14. The adjustable orthodontic appliance as recited in claim 12, wherein the bracket defines an opening through which an instrument can be inserted into the hollow cavity and pressed against the at least one leaf spring in order to manually compressed the at least one leaf spring.

15. The adjustable orthodontic appliance as recited in claim 12, wherein the bracket is pivotally connected to the base at a ball-and-socket joint such that, when the at least one leaf spring is manually compressed, the bracket and the base remain pivotally connected.

16. The adjustable orthodontic appliance as recited in claim 12, wherein each of the at least one leaf spring is pivotally connected to a hinged fulcrum that is attached to the bracket.

17. The adjustable orthodontic appliance as recited in claim 12, wherein the one or more pins engage the mesh surface by a magnetic force between the one or more pins and the mesh surface.

18. An adjustable orthodontic appliance comprising:
- a base comprising at least one surface adapted to be attached to a tooth and at least one mesh surface;
- a bracket comprising one or more notches adapted to receive an arch wire; and
- a spring-loaded locking mechanism attached the bracket, the spring-loaded locking mechanism comprising:
  - at least one helical compression spring; and
  - one or more pins operably connected to the at least one helical compression spring,
- wherein the at least one helical compression spring, when naturally uncompressed, causes the one or more pins to engage with the mesh surface of the base thereby locking the position of the bracket in place with respect to the position of the base, and
- wherein the at least one helical compression spring, when manually compressed, causes the one or more pins to disengage from the mesh surface of the base, thereby allowing the position of the bracket to be adjusted with respect to the position of the base.

19. The adjustable orthodontic appliance as recited in claim 18, wherein the bracket further comprises one or more wings for attaching elastic bands in order to maintain the arch wire in the one or more notches.

20. The adjustable orthodontic appliance as recited in claim 18, wherein the bracket defines an opening through which an instrument can be inserted and pressed against the at least one helical compression spring in order to manually compressed the at least one helical compression spring.

21. The adjustable orthodontic appliance as recited in claim 18, wherein the bracket is pivotally connected to the base at a cufflink joint such that, when the at least one helical compression spring is manually compressed, the bracket and the base remain pivotally connected.

22. The adjustable orthodontic appliance as recited in claim 18, wherein each of the one or more pins is connected to a lever arm and the lever arm is connected to the at least one helical compression spring, the lever arm also being connected to a hinged fulcrum that is attached to the bracket.

23. The adjustable orthodontic appliance as recited in claim 18, wherein the one or more pins engage the mesh surface by a magnetic force between the one or more pins and the mesh surface.

* * * * *

UNITED STATES PATENT AND TRADEMARK OFFICE
CERTIFICATE OF CORRECTION

PATENT NO.         : 7,431,586 B1                                    Page 1 of 1
APPLICATION NO.    : 11/437199
DATED              : October 7, 2008
INVENTOR(S)        : Silverman It is certified that error appears in the above-identified patent and that said Letters Patent is hereby corrected as shown below:

Column 4
Line 10, change "appliances" to --appliance--

Column 5
Line 6, change "socket 232" to --socket 234--
Line 20, change "post 219" to --post 218--
Line 41, change "pins 214" to --pins 212--
Line 63, change "appliances" to --appliance--
Line 66-67, change "tooth 302." to --tooth.--

Column 6
Line 21, change "tooth 302," to --tooth,--
Line 33, change "hollow cavity" to --hollow cavity 340--

Column 7
Line 8, change "attached the post 318" to --attached to the post 318--
Line 12, change "four lever arms 338" to --four lever arms 328 and 338--
Line 20, change "Figs. 2A – 3A" to --Figs. 2A – 2E--

Column 8, Claim 8, Line 8, change "unlock" to --unlocked--
Column 8, Claim 14, Line 58, change "compressed" to --compress--
Column 10, Claim 20, Line 9, change "compressed" to --compress--

Signed and Sealed this

Eighth Day of December, 2009

David J. Kappos
*Director of the United States Patent and Trademark Office*